United States Patent [19]
Filippini et al.

[11] Patent Number: 5,989,869
[45] Date of Patent: Nov. 23, 1999

[54] PROCESS FOR PREPARING DAUNORUBICIN AND DOXORUBICIN

[75] Inventors: Silvia Filippini, Milan, Italy; Natalia Lomovskaya; Leonid Fonstein, both of Madison, Wis.; Anna Luisa Colombo, Milan, Italy; C. Richard Hutchinson, Cross Plains, Wis.

[73] Assignee: Pharmacia & Upjohn S.p.A., Nerviano, Italy

[21] Appl. No.: 08/812,412

[22] Filed: Mar. 6, 1997

[51] Int. Cl.$^6$ .............................. C12P 19/56; C12N 1/20; C07H 21/02

[52] U.S. Cl. ...................... 435/78; 435/252.35; 536/23.1

[58] Field of Search ................................. 435/78, 252.35; 536/23.1

[56] References Cited

PUBLICATIONS

Hutchinson, C. et al., Antonie van Leeuwenhoek, vol. 64, pp. 165–176, 1993.
Scotti, C. et al., J. Bacter., vol. 178, pp. 7316–7321, Dec. 1996.

*Primary Examiner*—Ponnathapu Achutamurthy
*Assistant Examiner*—Peter P. Tung
*Attorney, Agent, or Firm*—Nikaido Marmelstein Murray & Oram, LLP

[57] ABSTRACT

The present invention is directed to a process for improving daunorubicin and doxorubicin production by means of a recombinant microorganism in which a gene of daunorubicin metabolism involved in the glycosylation of daunorubicin to acid-sensitive, baumycin-like compounds is inactivated.

2 Claims, 2 Drawing Sheets

5,989,869

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1401 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Streptomyces peucetius (ix) FEATURE:
      (A) NAME/KEY: CDS
      (B) LOCATION:190..1398

(xi) SEQUENCE DESCRIPTION: SEQ ID NO: 1:

```
AGTACTGCCA GATCGAGCGG CTGGGGAACC TGGCCGCGCT GCCGGGGTGC GACGGCTTCC        60

AGGTCGCCTG CTTCCCCGTG AAGATCACCG GCGGGGGGGC CGGCTGGACC CGCGCGGTCG       120

CCTTCGTCGA CGAATGAACG TTCCGGGCGG TGGCCCCGGA CCGGCGGCCA CTCAGCATCG       180

AGAGGGATC ATG GAG CCG AAC GAA TCG ACA TGT CGT ATC TGC GGT GGC          228
           Met Glu Pro Asn Glu Ser Thr Cys Arg Ile Cys Gly Gly
             1               5                  10
```

```
CGA GTA CGG GAG TTC TTC GAC TTC GGC CGC CAG CCG CTG TCC GAC TAC      276
Arg Val Arg Glu Phe Phe Asp Phe Gly Arg Gln Pro Leu Ser Asp Tyr
 15                  20                  25

TTC CCG TCG GAG GAG GAG CTC GAC AAC GAG TTC TTC TTC CGG CTC GCG      324
Phe Pro Ser Glu Glu Glu Leu Asp Asn Glu Phe Phe Phe Arg Leu Ala
 30                  35                  40                  45

GTC GGG ATG TGC GTC ACG TGC ACC ATG GTC CAG CTG CTG GAG GAG GTG      372
Val Gly Met Cys Val Thr Cys Thr Met Val Gln Leu Leu Glu Glu Val
                 50                  55                  60

CCC AGG GAC CGC ATG TTC CGC TAC GAC TAC CCG TAC CAC TCG TCG GGG      420
Pro Arg Asp Arg Met Phe Arg Tyr Asp Tyr Pro Tyr His Ser Ser Gly
                 65                  70                  75

TCG GAG CGG ATG CGC GAG CAC TTC GCG GCG ACC GCC CGC CGG CTG ATC      468
Ser Glu Arg Met Arg Glu His Phe Ala Ala Thr Ala Arg Arg Leu Ile
         80                  85                  90

GGC ACC GAG CTG ACC GGG CGG GAC CCG TTC TGC GTG GAG ATC GGC AGC      516
Gly Thr Glu Leu Thr Gly Arg Asp Pro Phe Cys Val Glu Ile Gly Ser
         95                 100                 105

AAC GAC GGA GTG ATG CTC CGC ACG GTG CGC GAC GCC GGT GTC CGA CAC      564
Asn Asp Gly Val Met Leu Arg Thr Val Arg Asp Ala Gly Val Arg His
110                 115                 120                 125

CTG GGC GTG GAG CCT TCC GGC GGT GTC GCC GAC GTG TCC CGG GCC GAG      612
Leu Gly Val Glu Pro Ser Gly Gly Val Ala Asp Val Ser Arg Ala Glu
                130                 135                 140

GGC ATC CAG GTG CGG ACC GCG TTC TTC GAG GAG TCC ACG GCC CGG GAG      660
Gly Ile Gln Val Arg Thr Ala Phe Phe Glu Glu Ser Thr Ala Arg Glu
                145                 150                 155

ATC GCC CAG GAA CAC GGG CCC GCG AAC GTC ATC TAC GCG GCC AAC ACG      708
Ile Ala Gln Glu His Gly Pro Ala Asn Val Ile Tyr Ala Ala Asn Thr
        160                 165                 170

ATC TGT CAT ATC CCG TAC CTC GAC TCC GTC TTC CGC GGT ATC GAC GCC      756
Ile Cys His Ile Pro Tyr Leu Asp Ser Val Phe Arg Gly Ile Asp Ala
        175                 180                 185

CTC CTC GCG CCG GAC GGC GTC TTC GTC TTC GAG GAC CCC TAC CTC GGC      804
Leu Leu Ala Pro Asp Gly Val Phe Val Phe Glu Asp Pro Tyr Leu Gly
190                 195                 200                 205

GAC ATC GTC GAG AAG AAC ACC TTC GAC CAG ATC TAC GAC GAG CAC TTC      852
Asp Ile Val Glu Lys Asn Thr Phe Asp Gln Ile Tyr Asp Glu His Phe
                210                 215                 220

TAC CTG TTC ACC GCC CGC TCG GTG AGC ACC ACC GCC CAG CAC TTC GGA      900
Tyr Leu Phe Thr Ala Arg Ser Val Ser Thr Thr Ala Gln His Phe Gly
                225                 230                 235

TTC GAA CTG GTC GAC GTG GAG CGG CTC CCG GTG CAC GGC GGC GAG GTC      948
Phe Glu Leu Val Asp Val Glu Arg Leu Pro Val His Gly Gly Glu Val
        240                 245                 250

CGC TAC ACC ATC GCC CGC GCG GGC CGG CGG CAG CCG AGC CCC CGG GTC      996
Arg Tyr Thr Ile Ala Arg Ala Gly Arg Arg Gln Pro Ser Pro Arg Val
        255                 260                 265

GGC GAG CTC ATC GCC GAG GAG AGC CGG CGC GGG CTC GCC GAC CTG ACG     1044
Gly Glu Leu Ile Ala Glu Glu Ser Arg Arg Gly Leu Ala Asp Leu Thr
270                 275                 280                 285

ACG CTG GAG AAG TTC GGC GCC CAG GTC AAG CGG GTC TGC TGT GAC CTG     1092
Thr Leu Glu Lys Phe Gly Ala Gln Val Lys Arg Val Cys Cys Asp Leu
                290                 295                 300

GTG GCC CGT CTG CGC GAG CTG CGC GAC CTC GGC TTC TAC GTC GTC GGG     1140
Val Ala Arg Leu Arg Glu Leu Arg Asp Leu Gly Phe Tyr Val Val Gly
                305                 310                 315

TAC GGG GCG ACC GCC AAG AGC GCC ACA GTG CTC AAC TAT GCG GGG ATC     1188
Tyr Gly Ala Thr Ala Lys Ser Ala Thr Val Leu Asn Tyr Ala Gly Ile
                320                 325                 330
```

```
GGC CCC GAT CTG CTG CCG TGC GTC TAC GAC ACC ACG CCG GCC AAG ATC      1236
Gly Pro Asp Leu Leu Pro Cys Val Tyr Asp Thr Thr Pro Ala Lys Ile
    335                 340                 345

GGC CGT CGG CTC CCC GGG TCC CAC ATC CCC ATC CGC TCC GCC GAG GAG      1284
Gly Arg Arg Leu Pro Gly Ser His Ile Pro Ile Arg Ser Ala Glu Glu
350                 355                 360                 365

TTC CGG GCC CCC TAC CCC GAC TAT GCG CTG CTC TTC GCC TGG AAC CAC      1332
Phe Arg Ala Pro Tyr Pro Asp Tyr Ala Leu Leu Phe Ala Trp Asn His
                370                 375                 380

CTA GAC GAA GTC CAG GCC CGA GAG GCG GAG TTC ACG AAG CAG GGG GGC      1380
Leu Asp Glu Val Gln Ala Arg Glu Ala Glu Phe Thr Lys Gln Gly Gly
            385                 390                 395

CGC TGG ATC CGC TCA GGG TGA                                          1401
Arg Trp Ile Arg Ser Gly
            400
```

(2) INFORMATION FOR SEQ ID NO: 2:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Pro Asn Glu Ser Thr Cys Arg Ile Cys Gly Gly Arg Val Arg
1               5                   10                  15

Glu Phe Phe Asp Phe Gly Arg Gln Pro Leu Ser Asp Tyr Phe Pro Ser
            20                  25                  30

Glu Glu Glu Leu Asp Asn Glu Phe Phe Arg Leu Ala Val Gly Met
        35                  40                  45

Cys Val Thr Cys Thr Met Val Gln Leu Leu Glu Glu Val Pro Arg Asp
    50                  55                  60

Arg Met Phe Arg Tyr Asp Tyr Pro Tyr His Ser Ser Gly Ser Glu Arg
65                  70                  75                  80

Met Arg Glu His Phe Ala Ala Thr Ala Arg Arg Leu Ile Gly Thr Glu
                85                  90                  95

Leu Thr Gly Arg Asp Pro Phe Cys Val Glu Ile Gly Ser Asn Asp Gly
            100                 105                 110

Val Met Leu Arg Thr Val Arg Asp Ala Gly Val Arg His Leu Gly Val
        115                 120                 125

Glu Pro Ser Gly Gly Val Ala Asp Val Ser Arg Ala Glu Gly Ile Gln
    130                 135                 140

Val Arg Thr Ala Phe Phe Glu Glu Ser Thr Ala Arg Glu Ile Ala Gln
145                 150                 155                 160

Glu His Gly Pro Ala Asn Val Ile Tyr Ala Ala Asn Thr Ile Cys His
                165                 170                 175

Ile Pro Tyr Leu Asp Ser Val Phe Arg Gly Ile Asp Ala Leu Leu Ala
            180                 185                 190

Pro Asp Gly Val Phe Val Phe Glu Asp Pro Tyr Leu Gly Asp Ile Val
        195                 200                 205

Glu Lys Asn Thr Phe Asp Gln Ile Tyr Asp Glu His Phe Tyr Leu Phe
    210                 215                 220

Thr Ala Arg Ser Val Ser Thr Ala Gln His Phe Gly Phe Glu Leu
225                 230                 235                 240

Val Asp Val Glu Arg Leu Pro Val His Gly Glu Val Arg Tyr Thr
            245                 250                 255
```

-continued

```
Ile Ala Arg Ala Gly Arg Arg Gln Pro Ser Pro Arg Val Gly Glu Leu
            260                 265                 270

Ile Ala Glu Glu Ser Arg Arg Gly Leu Ala Asp Leu Thr Thr Leu Glu
            275                 280                 285

Lys Phe Gly Ala Gln Val Lys Arg Val Cys Cys Asp Leu Val Ala Arg
            290                 295             300

Leu Arg Glu Leu Arg Asp Leu Gly Phe Tyr Val Val Gly Tyr Gly Ala
305                     310                 315                 320

Thr Ala Lys Ser Ala Thr Val Leu Asn Tyr Ala Gly Ile Gly Pro Asp
                325                 330                 335

Leu Leu Pro Cys Val Tyr Asp Thr Thr Pro Ala Lys Ile Gly Arg Arg
                340                 345             350

Leu Pro Gly Ser His Ile Pro Ile Arg Ser Ala Glu Glu Phe Arg Ala
            355                 360             365

Pro Tyr Pro Asp Tyr Ala Leu Leu Phe Ala Trp Asn His Leu Asp Glu
        370                 375             380

Val Gln Ala Arg Glu Ala Glu Phe Thr Lys Gln Gly Gly Arg Trp Ile
385                 390                 395                 400

Arg Ser Gly
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            primer"

(xi) SEQUENCE DESCRIPTION: SEQ ID NO: 3:

CGCCAGGGTT TTCCCAGTCA CGAC          24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            primer"

(xi) SEQUENCE DESCRIPTION: SEQ ID NO: 4:

AGCGGATAAC AATTTCACAC AGGA          24

PROCESS FOR PREPARING DAUNORUBICIN AND DOXORUBICIN

FIELD OF THE INVENTION

The present invention concerns a process for improving daunorubicin and doxorubicin production by means of a recombinant strain bearing a mutation inactivating a gene of daunorubicin metabolism involved in the glycosylation of daunorubicin to acid-sensitive, baumycin-like compounds.

BACKGROUND OF THE INVENTION

Anthracyclines of the daunorubicin group such as doxorubicin, carminomycin and aclacinomycin and their synthetic analogs are among the most widely employed agents in antitumoral therapy (F. Arcamone, *Doxorubicin*, Academic Press N.Y., 1981, pp. 12–25; A. Grein, *Process Biochem.*, 16:34, 1981; T. Kaneko, *Chimicaoggi* May 11, 1988; C. E. Myers et al., "Biochemical mechanism of tumor cell kill" in *Anthracycline and Anthracenedione-Based Anticancer Agents* (Lown, J. W., ed.) Elsevier Amsterdam, pp. 527–569, 1988; J. W. Lown, *Pharmac. Ther.* 60:185–214, 1993). Anthracyclines of the daunorubicin group are naturally occurring compounds produced by various strains of Streptomyces and by *Actinomyces carminata*. Doxorubicin is mainly produced by strains of *S. peucetius* while daunorubicin is produced by many other Actinomycetes. In particular daunorubicin and doxorubicin are synthesized in *Streptomyces peucetius* ATCC 29050 and 27952 from malonic acid, propionic acid and glucose by the pathway summarized in Grein, *Advan. Applied Microbiol.* 32;203, 1987 and in Eckart and Wagner, *J. Basic Microbiol.* 28:137, 1988. Aklavinone (11-deoxy-ε-rhodomycinone), ε-rhodomycinone and carminomycin are established intermediates in this process. The final step in this pathway involves the hydroxylation of daunorubicin to doxorubicin, which is reported to occur only in *S. peucetius* species.

Daunorubicin is known to be converted to 4'-O-glycosides called baumycins in Streptomyces species (Y. Takahashi, H. Naganawa. T. Takeuchi, H. Umezawa, T. Komiyama, T. Oki and T. Inui. *J. Antibiot.* 30:622, 1977) thus decreasing also the amount of doxorubicin potentially obtainable through oxidation of daunorubicin. For recovering daunorubicin at the end of fermentation, baumycins are converted to daunorubicin by acid hydrolysis. However this process presents certain drawbacks in that the amount of doxorubicin thus produced is low and the process is complicated by the acid hydrolysis step. The present invention solves this problem by providing a mutated Streptomyces strain in which one of the genes responsible for the conversion of daunorubicin to baumycins has been insertionally inactivated.

SUMMARY OF THE INVENTION

The present invention provides a process for preparing daunorubicin and doxorubicin by means of a bacterial recombinant strain bearing a mutation inactivating the function of a gene of daunorubicin metabolism involved in the glycosylation of daunorubicin to acid-sensitive baumycin-like compounds. The inactivating mutation increases daunorubicin and doxorubicin production levels and causes the disappearance of baumycin-like products resulting in daunorubicin and doxorubicin secretion directly into the culture medium. Consequently, there is no need to acidify the cultures at the end of fermentation. Preferably the bacterial strain is a strain of Streptomyces sp. producing daunorubicin and also doxorubicin, having a mutation inactivating the function of a gene of daunorubicin metabolism. Said inactivated gene is preferably comprised in the DNA fragment having the configuration of restriction sites shown in FIG. 1 or in a fragment derived therefrom containing a gene, dnrX, encoding for a protein involved in the metabolism of daunorubicin to acid-sensitive, baumycin-like compounds. Thus, the present invention provides a mutant strain of *S. peucetius*, obtained from *S. peucetius* ATCC 29050, having a mutation inactivating the function of the dnrX gene. A cluster of genes for daunorubicin and doxorubicin biosynthesis and resistance have been obtained from *S. peucetius* 29050 and *S. peucetius* 27952 by cloning experiments as described in Stutzman-Engwall and Hutchinson (*Proc. Natl. Acad. Sci. U.S.A.* 86: 3135 (1988)) and Otten et al., (*J. Bacteriol.* 172: 3427 (1990)). As explained in more details in the following description, the dnrX mutant was obtained disrupting the dnrX gene of the anthracycline biosynthetic gene cluster by insertion of the neomycin/kanamycin resistance gene (aphII) in the NcoI restriction site of dnrX.

Figure 1:
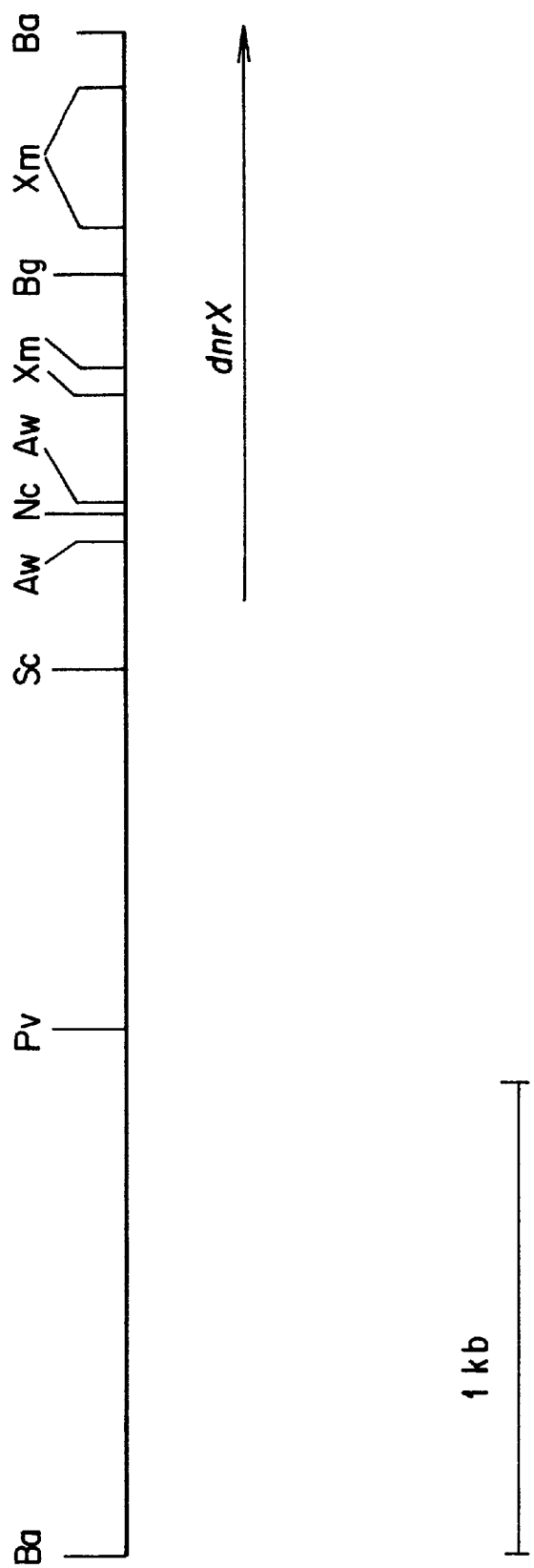
FIG. 1 is a restriction map analysis of the DNA of the invention. Said DNA is a BamHI fragment of 3.3 kb, containing the dnrX gene, obtained from the cosmid clone pWHM335 described in Stutzman-Engwall and Hutchinson (*Proc. Natl. Acad. Sci. U.S.A.* 86: 3135 (1988)) and Otten et al., (*J. Bacteriol.* 172: 3427 (1990)). The fragment was inserted into the unique BamHI restriction site of the polylinker region of plasmid pUC19 (Yanish-Perron C. et al., *Gene* 33:103–119 (1985)). The map shown in FIG. 1 does not necessarily provide an exhaustive listing of all restriction sites present in the DNA fragment. However, the reported sites are sufficient for an unambiguous recognition of the DNA segment. [Restriction site abbreviations: Ba, BamHI; Nc, NcoI; Sc, ScaI; Xm, XmaI; Aw, AlwNI; Bg, BglII; Pv, PvuI.]

SEQ ID NO:1 is a schematic illustration of the dnrX DNA nucleotide sequence. Said DNA corresponds to that encoding a protein required for daunorubicin metabolism. The sequence covers the region between the ScaI and the BamHI restriction sites and shows the coding strand in the 5' to 3' direction. The derived amino acid sequence of the translated open reading frame encoding a protein required for daunorubicin glycosylation is shown under SEQ ID NO:2.

DESCRIPTION OF THE INVENTION

The present invention provides a bacterial recombinant strain bearing a mutation inactivating the function of the daunorubicin metabolism gene dnrX involved in the glycosylation of daunorubicin to acid-sensitive baumycin-like compounds.

The bacterial strain may be one that is daunorubicin- or doxorubicin-sensitive, i.e. cannot grow in the presence of a certain amount of daunorubicin or doxorubicin, or that is daunorubicin- or doxorubicin-resistant. Strains belonging to the Streptomyces genus constitute a preferred embodiment of the invention; a *Streptomyces peucetius* strain constitutes a particularly preferred embodiment of the invention. Most preferred is the *S. peucetius* strain WMH1654. The strain WMH1654 has been deposited at the American Type Culture Collection, Rockville, Md., USA, under the accession number ATCC 55936.

Strain WMH1654 has been obtained from the *S. peucetius* ATCC 29050 strain by replacing the dnrX gene with a mutated dnrX gene insertionally inactivated by introduction of the neomycin/kanamycin resistance gene (aphII) from pFDNEO-S plasmid described by F. Danis and R. Brzezinski, (*FEMS Microbiology Letters* 81:261–264 (1991)). The aphII gene has been inserted at the NcoI site of dnrX to disrupt its function, as better explained in Example 1.

The expert in the art will recognize that any other technique to inactivate the gene can be suitably employed in the present invention.

The bacterial recombinant strain may be any other microorganism transformed with plasmids or transfected with phage DNA containing an anthracycline gene cluster able to produce daunorubicin and/or doxorubicin and/or baumycins.

In another aspect, the present invention provides a process for preparing daunorubicin and doxorubicin, which process comprises:
(i) culturing a bacterial recombinant strain of the invention, and
(ii) isolating daunorubicin and doxorubicin from the culture.

In this process the bacterial recombinant strain may be cultured at from 20 to 40° C., for example from 26 to 37° C. The culture is preferably carried out with agitation. In order to obtain the bacterial recombinant strain of the invention, the dnrX gene was isolated from clones described in Stutzman-Engwall and Hutchinson, (*Proc. Acad. Sci. USA* 86:3135 (1989) and Otten et al., (*J. Bacteriol.* 172:3427 (1990). The gene dnrX is contained in a 3.3 kb DNA fragment obtained by digestion of the clone pWHM335 with the restriction endonuclease BamHI.

The dnrX gene consists essentially of the sequence of SEQ. ID NO. 1, which sequence will be referred to as the "dnrX" sequence. The deduced amino acid sequence of the daunorubicin and doxorubicin metabolism protein encoded by SEQ. ID NO. 1 is shown in SEQ. ID NO. 2. The isolated dnrX gene was subsequently subcloned into an appropriate DNA cloning vector. Any autonomously replicating and/or integrating agent comprising a DNA molecule to which one or more additional DNA segments can be added may be used. Typically, however, the vector is a plasmid. Preferred plasmids are pUC19 (Yanish-Perron et al., Gene 33: 103 (1985)) and pWHM3 (Vara et al., J. Bacteriol. 171:5872 (1989)). Any suitable technique may be used to insert the insert DNA into the vector. Insertion can be achieved by ligating the DNA into a linearized vector at an appropriate restriction site. For this, direct combination of sticky or blunt ends, homopolymer tailing, or the use of a linker or adapter molecule may be employed. The recombinant plasmid is then digested with a suitable restriction enzyme and ligated with the aphII gene. This construction is transferred into a suitable vector for homologous integration. Among the possible vectors that can be used, pKC1139 (M. Bierman et al., Gene 116:43–49 (1992)) is preferred. This is an *E. coli*-Streptomyces shuttle vector that contains a temperature-sensitive replicon that functions well at temperature below 34° C. and bears the apramycin resistance gene. The recombinant vector thus obtained is used to transform, typically by protoplast transformation, an appropriate Streptomyces strain; the final step in this inactivation protocol is the isolation of kanamycin resistant transformant in which the recombinant plasmid has recombined with the dnrX gene and inactivated it (see also Example 1).

On the basis of the information provided herein, the expert in the art can easily obtain the 3.3 kb BamHI DNA fragment by:
a) preparing a library of the genomic DNA of *S. peucetius* 29050 or a strain derived therefrom;
b) screening the library for clones positive to a labelled probe, of at least 24 nucleotides, synthesized according to the sequence of SEQ ID NO: 1;
c) obtaining an insert DNA, from a recombinant vector, that forms part of the library and that has been screened as positive for the ability to convert daunorubicin into the acid-sensitive metabolite form in the *S. peucetius* dnrX mutant.

To obtain the DNA fragment, the library may be prepared in step a) by partially digesting the genomic DNA of *S. peucetius* 29050 or a strain derived therefrom; or by screening a library of Streptomyces genomic DNA that has been enriched for the cluster of daunorubicin/doxorubicin biosynthesis genes. Generally the restriction enzyme MboI is preferably used for genomic DNA, but for the libraries containing the cluster of daunorubicin biosynthesis genes, the restriction enzyme BamHI is preferred. The DNA fragments thus obtained can be size fractionated; fragments from 1 to 7 kb in size are preferred for libraries containing the cluster of daunorubicin and doxorubicin biosynthesis genes. These fragments are ligated into a linearized vector such as pWHM3 or pKC505 ((M. A. Richardson et al, *Gene* 61:231 (1987)). *E.coli* DH5α and DH1 are respectively transformed or transfected with the ligation mixtures.

In step b) the colonies obtained by the transformantion are transferred to nylon membranes and screened by colony hybridization for plasmids or cosmids which hybridized to the labelled probe, of at least 24 nucleotides, synthesized according to the sequence of SEQ ID No. 1

In step c) plasmid DNA from the clones which hybridized to the probe is isolated and used to transform protoplasts of host cells. The hosts may be microorganisms that do not produce acid-sensitive, baumycin-like products. The *S. peucetius* dnrX mutant strain (ATCC 55936) that does not produce acid-sensitive, baumycin-like compounds represents a particularly suitable host. Clones containing DNA fragments which include the 3.3 kb BamHI DNA fragment of the invention are recognized by the appearance in non-acidified fermentation cultures of acid-sensitive, baumycin-like compounds.

MATERIALS AND METHODS

Bacterial strains and plasmids:

*E. coli* strains DH5α or JM109, which are sensitive to ampicillin and apramycin, are used for subcloning DNA fragments. *S. peucetius* dnrX mutant that does not produce acid-sensitive daunorubicin metabolites is used for expression of the dnrX gene. The plasmid cloning vectors are pUC18/19 ((Yanish-Perron et al., Gene 33:103 (1985)) and pWHM3 (Vara et al., *J. Bacteriol.* 171:5872 (1989)). The vector for homologous integration is pKC1139 (M. Bierman et al., Gene 116:43–49 (1992)), a shuttle *E. coli*-Streptomyces vector. The pFDNEO-S plasmid described by F. Danis and R. Brzezinski (FEMS Microbiology Letters 81:261–264 (1991)) is used to get the neomycin/kanamycin resistance gene (aphII).

Media and buffer:

*E. coli* strains DH5α and JM109 are maintained on LB agar (Sambrook et al., *Molecular cloning. A laboratory Manual,* 2nd ed. Cold Spring Harbor Press, Cold Spring Harbor, N.Y., 1989). When selecting for transformants, ampicillin or apramycin are added at concentrations of 100 micrograms/ml and 50 micrograms/ml, respectively. *S. peu-*

*cetius* dnrX is maintained on ISP4 agar (Difco Laboratories, Detroit, Mich.) for the preparation of spores and on R2YE agar (Hopwood et al., *Genetic Manipulation of Streptomyces. A Laboratory Manual,* John Innes Foundation, Norwich, UK, 1985) for regeneration of protoplasts. When selecting for transformants, the plates are overlayed with soft agar containing 350 micrograms/ml apramycin corresponding to a final concentration in the plates of 40 micrograms/ml apramycin.

Subcloning DNA fragments:

DNA samples are digested with appropriate restriction enzymes and separated on an agarose gel by standard methods (Sambrook et al., *Molecular cloning. A Laboratory Manual,* 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.) or an equivalent. The isolated DNA fragments are subcloned using standard techniques (Sambrook et al., *Molecular cloning. A Laboratory Manual,* 2nd ed. Cold Spring Harbor Press, Cold Spring Harbor, N.Y., 1989) into *E. coli* for routine manipulations, including DNA sequencing, and *E. coli*-Streptomyces shuttle vectors or Streptomyces vectors for expression experiments and fermentations.

DNA sequencing of the dnrX gene.

In order to sequence the fragment containing the gene of interest, the following synthetic oligonucleotide primers for pUC19 have been synthesized:

pUC Sequencing Primer (−47) 24-mer:

5'd(CGCCAGGGTTTTCCCAGTCACGAC)3'   (SEQ ID NO:3);

PUC Reverse Sequencing (−48) 24-mer:

5'd(AGCGGATAACAATTTCACACAGGA)3'   (SEQ ID NO:4).

The sequence determination has been performed simultaneously on both strands.

Transformation of Streptomyces species and *E. coli:*

Competent cells of *E. coli* are prepared by the calcium chloride method (Sambrook et al., *Molecular cloning. A Laboratory Manual,* 2nd ed. Cold Spring Harbor Press, Cold Spring Harbor, N.Y., 1989) and transformed by standard techniques (Sambrook et al., *Molecular cloning. A Laboratory Manual,* 2nd ed. Cold Spring Harbor Press, Cold Spring Harbor, N.Y., 1989). *S. peucetius* 29050 or *S. peucetius* dnrX mycelium is grown in R2YE medium (Hopwood et al., *Genetic Manipulation of Streptomyces. A Laboratory Manual,* John Innes Foundation, Norwich, UK, 1985) and harvested after 48 hr. The mycelial pellet is washed twice with 10.3% (wt/vol) sucrose solution and used to prepare protoplasts according to the method outlined in the Hopwood manual (Hopwood et al., *Genetic Manipulation of Streptomyces. A Laboratory Manual,* John Innes Foundation, Norwich, UK, 1985). The protoplast pellet is suspended in about 300 microlitres of P buffer (Hopwood et al., *Genetic Manipulation of Streptomyces. A Laboratory Manual,* John Innes Foundation, Norwich, UK, 1985) and a 50 microlitre aliquot of this suspension is used for each transformation. Protoplasts are transformed with plasmid DNA according to the small scale transformation method of Hopwood et al.. (Hopwood et al., *Genetic Manipulation of Streptomyces. A Laboratory Manual,* John Innes Foundation, Norwich, UK, 1985), Stutzman-Engwall and Hutchinson, (*Proc. Natl. Acad. Sci. U.S.A.* 86: 3135 (1988) or Otten et al. (Otten et al., *J. Bacteriol.* 172:3427 (1990)). After 17 hr of regeneration on R2YE medium at 30° C., the plates are overlayed with 40 micrograms/ml of apramycin and allowed to grow at 30° C. until sporulated.

Doxorubicin and daunorubicin production:

*S. peucetius* dnrX mutant strain is inoculated into 25 ml of liquid R2YE medium with 40 micrograms/ml of kanamycin sulfate in a 300 ml flask and incubated at 30° C. and 300 rpm on a rotary shaker. After 2 days of growth 2.5 ml of this culture are transferred to 25 ml of APM production medium: ((g/l) glucose (60), yeast extract (8), malt extract (20), NaCl (2), 3-(morpholino)propanesulfonic acid (MOPS) sodium salt (15), $MgSO_4$ $0.7H_2O$ (0.2), $FeSO_4$ $0.7H_2O$ (0.01), $ZnSO_4 0.7H_2O$ (0.01), and incubated in a 300 ml flask at 30° C. and 300 rpm on a rotary shaker for 120 hr. Each culture is divided in two aliquots of 10 g each: one is acidified with 250 mg oxalic acid and incubated at 30° C. overnight and then extracted. The other is immediately extracted. Cultures are extracted with an equal volume of acetonitrile:methanol (1:1) at 30° C. and 300 rpm for 2 hr. The extract is filtered and the filtrate is analyzed by reversed-phase high pressure liquid chromatography (RP-HPLC). RP-HPLC is performed by using a Vydac $C_{18}$ column (4.6×250 mm; 5 micrometers particle size) at a flow rate of 0.385 ml/min. Mobile phase A is 0.2% trifluoroacetic acid (TFA, from Pierce Chemical Co.) in $H_2O$ and mobile phase B is 0.078% TFA in acetonitrile (from J: T: Baker Chemical Co.). Elution is performed with a linear gradient from 20 to 60% phase B in phase A in 33 minutes and monitored with a diode array detector set at 488 nm (bandwith 12 micrometers). Daunorubicin and doxorubicin (10 micrograms/ml in methanol) are used as external standards to quantitate the amount of these metabolites isolated from the cultures.

EXAMPLE 1

Figure 2:
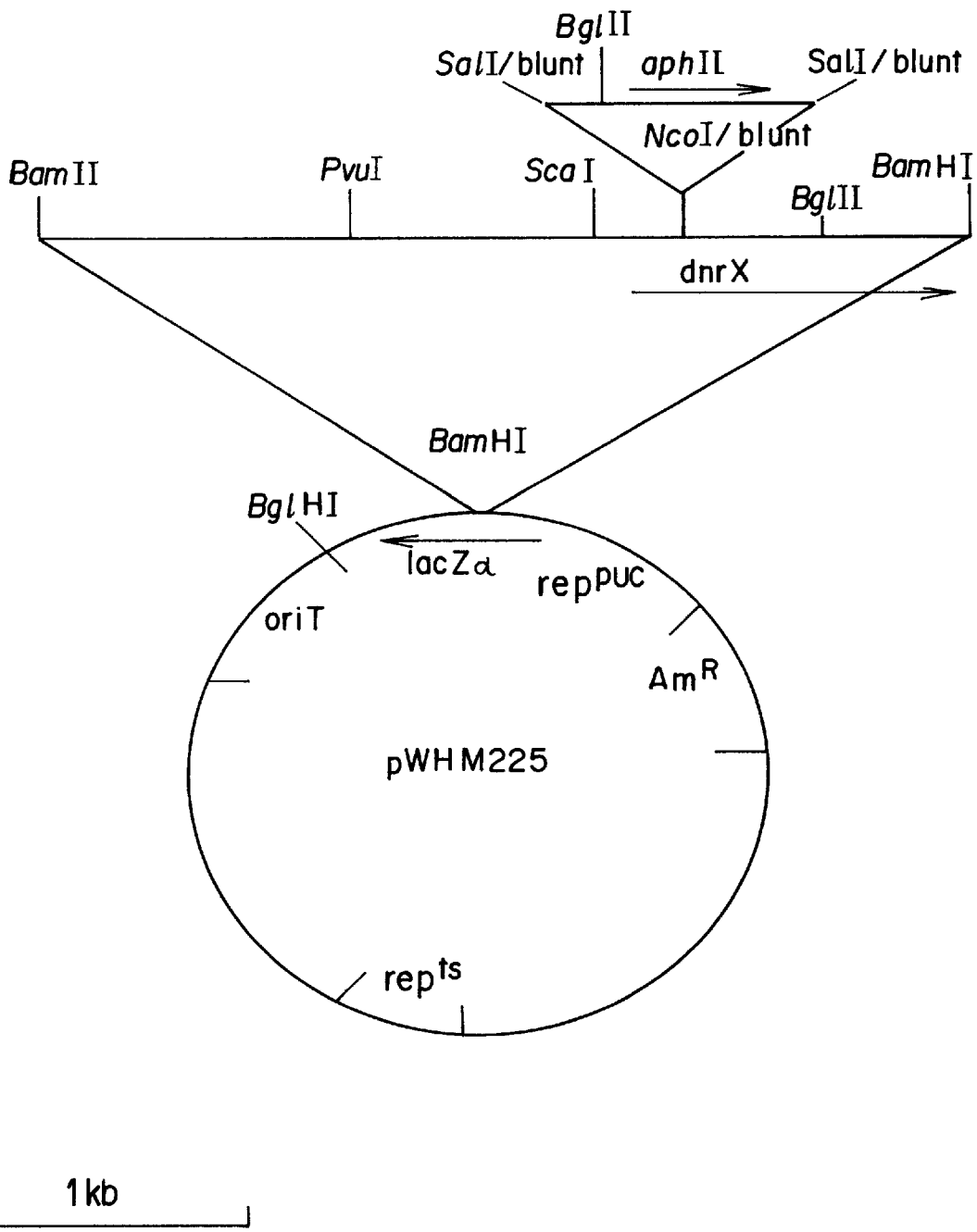
FIG. 2 is a representation of plasmid pWHM225 in which the 4.3 kb EcoRI-NindIII fragment from plasmid pWHM223 is inserted in the EcoRI-HindIII sites of plasmid pKC1139. The construction of plasmid pWHM225 is described in Example 1. The map shown in FIG. 2 does not necessarily provide an exhaustive listing of all restriction sites present in the DNA molecule.

Disruption of dnrX:

pWHM223 is constructed by subcloning the 3.3 kb BamHI fragment obtained from the pWHM335 cosmid clone, described by Stutzman-Engwall and Hutchinson ((*Proc. Acad. Sci. USA* 86:3135 (1989)) and Otten et al. (*J. Bacteriol.* 172:3427 (1990)), in the BamHI site of pUC19. This recombinant plasmid is NcoI digested, filled in with the Klenow fragment and ligated with the blunt-ended SalI aphII gene from the pFDNEO-S plasmid described by F. Danis and R. Brzezinski, (*FEMS Microbiology Letters* 81:261–264 (1991)). This construction is transferred as an EcoRI-HindIII fragment into plasmid pKC1139 (M. Bierman et al., *Gene* 116:43–49 (1992)) to obtain pWHM225 (FIG. 2). The pKC1139 vector contains a temperature-sensitive replicon that functions well at temperature below 34° C. and bears the apramycin resistance gene. Protoplasts of 29050 strain are transformed with pWHM225, and transformants are selected with apramycin sulfate (40 micrograms/ml) at 30° C. Colonies from this transformation are transferred to ISP4 agar supplemented with kanamycin sulfate (40 micrograms/ml) and incubated at 39° C. for 7 days to eliminate the autonomous replicating vector and to select transformants in which homologous recombination between the cloned DNA and the chromosome has occurred. Three of these cultures are isolated on ISP4 agar with kanamycin sulfate (40 micrograms/ml) and incubated at 39° C. for 7 days. Plates with about 100 colonies are replicated on ISP4 with apramycin sulfate (40 micrograms/ml) and incubated at 39° C. for 7 days. Colonies that don't grow on apramycin are selected from kanamycin plates and checked in fermentation in presence of kanamycin. Two colonies with the kanamycin-resistance, apramycin-sensitive phenotype are examined by Southern analysis to verify the disruption of the dnrX gene. Chromosomal DNA from the 29050 strain and the two dnrX mutants is digested with BamHI and probed with a 500 bp internal fragment of the aphII gene from the pFDNEO-S. The probe hybridizes to 4.3 kb fragment for the two dnrX mutants, which is consistent with the insertion of the aphII resistance gene in the dnrX gene.

EXAMPLE 2

Enhanced doxorubicin and daunorubicin production and baumycin-like compounds disappearance in fermentation broth of dnrX mutant.

The dnrX mutant is grown for 10 days at 30° C. on slants of ISP4 agar medium added with 40 micrograms of kanamycin sulfate. The spores of this culture are collected and suspended in 300 ml Erlenmeyer flasks containing 25 ml of R2YE liquid medium containing 40 micrograms of kanamycin sulfate and the flasks are shaken for 2 days at 30° C. on a rotary shaker running at 300 rpm in a 5 cm diameter circle. 2.5 ml of this culture are used to inoculate 25 ml of APM medium containing 40 micrograms of kanamycin sulfate in 300 ml Erlenmeyer flasks. The flasks are incubated at 30° C. for 120 hr under the same conditions described for the seed cultures. The metabolites are extracted from the cultures according to the methods described in the Materials and Methods section. The production values are indicated in Tables 1, A and B wherein R.T. stands for Retention Time.

| Strain | daunorubicin μg/ml | doxorubicin μg/ml | baumycin-like R.T. 35.9 | baumycin-like R.T. 39.3 |
|---|---|---|---|---|
| Table 1A. Production values in non acidified cultures | | | | |
| ATCC 29050 | 6 | 9 | ++ | +++ |
| WMH1654 | 35 | 41 | – | – |
| Table 1B. Production values in acidified cultures | | | | |
| ATCC 29050 | 45 | 14 | – | – |
| WMH1654 | 36 | 41 | – | – |

EXAMPLE 3

Complementation of the dnrX mutation with the wild-type dnrX gene

To confirm that the disappearance of the baumycin-like products in the fermentation broth is due to dnrX disruption, the dnrX mutant is transformed with the pWHM226 containing, in the BamHI site of the polylinker of pWHM3, the 3.3 kb fragment of the invention including the dnrX. pWHM226 is introduced in the S. peucetius dnrX mutant by the protoplast-mediated transformation method described above, using thiostrepton (50 μg/ml) for selection of the recombinant strains. Transformants are checked for doxorubicin and daunorubicin production, in presence of thiostrepton (10 μg/ml), according to the fermentation conditions described in Materials and Methods. Extracts of the non-acidified fermentation broths of two transformants show in RP-HPLC the appearance of the two peaks with retention times of 35.9 and 39.3 min, respectively, corresponding to the two acid-sensitive, baumycin-like compounds, while extracts of the dnrX mutant fermentation broth obtained under the same conditions do not show these peaks.

What is claimed is:

1. A process for preparing at least one compound selected from the group consisting of daunorubicin and doxorubicin, comprising the steps of:

culturing a recombinant *Streptomyces peucetius* comprising a daunorubicin metabolism gene dnrX, wherein the function of the dnrX gene involved in glycosylation of daunorubicin to acid-sensitive baumycin-like compounds has been inactivated, and isolating at least one compound selected from the group consisting of daunorubicin and doxorubicin from the culture.

2. The process according to claim 1, wherein said *Streptomyces peucetius* is WMH1654, ATCC 55936.

* * * * *

UNITED STATES PATENT AND TRADEMARK OFFICE
CERTIFICATE OF CORRECTION

PATENT NO. : 5,989,869
DATED : November 23, 1999
INVENTOR(S) : Filippini et al.

It is certified that error appears in the above-identified patent and that said Letters Patent is hereby corrected as shown below:

Column 2,
Line 37, please delete "NindIII" and insert therefor, -- HindIII --

Figure 2,
Please delete:

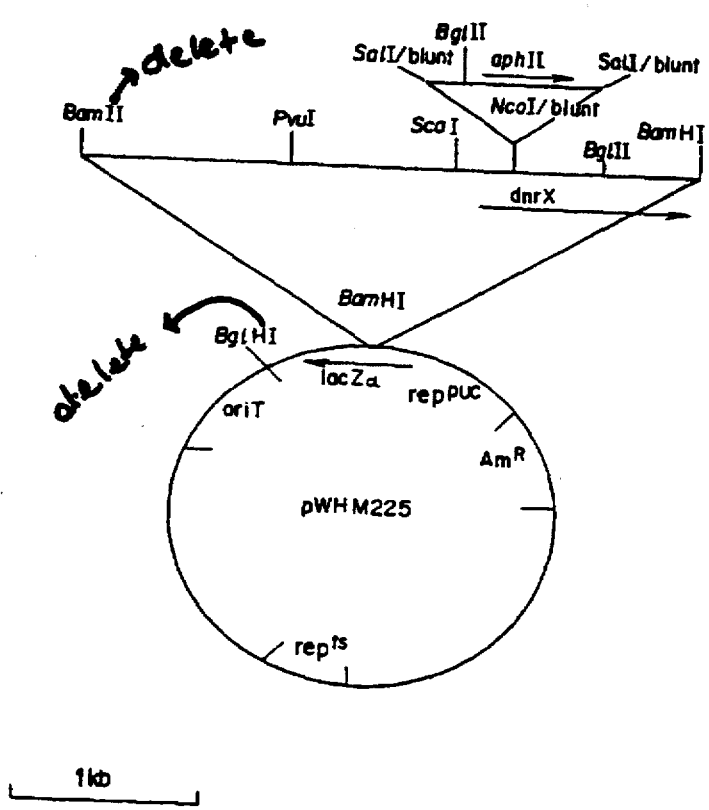

UNITED STATES PATENT AND TRADEMARK OFFICE
CERTIFICATE OF CORRECTION

PATENT NO. : 5,989,869
DATED : November 23, 1999
INVENTOR(S) : Filippini et al.

Page 2 of 2

It is certified that error appears in the above-identified patent and that said Letters Patent is hereby corrected as shown below:

and insert therefor,

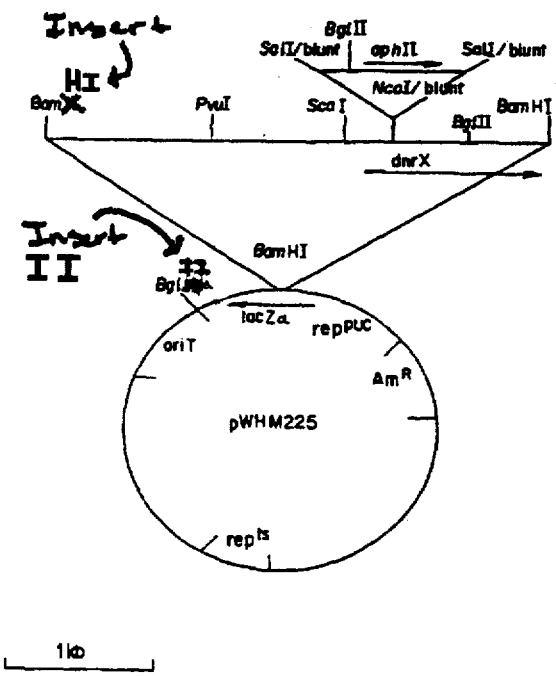

Signed and Sealed this

Eighth Day of January, 2002

JAMES E. ROGAN
Director of the United States Patent and Trademark Office